United States Patent [19]

Santoli et al.

[11] Patent Number: 5,272,082
[45] Date of Patent: Dec. 21, 1993

[54] CYTOTOXIC T-ALL CELL LINES AND USES THEREFOR

[75] Inventors: Daniela Santoli; Giovanni Rovera, both of Bryn Mawr; Alessandra Cesano, Philadelphia, all of Pa.

[73] Assignee: The Wistar Institute of Anatomy & Biology, Philadelphia, Pa.

[21] Appl. No.: 859,927

[22] Filed: Mar. 30, 1992

[51] Int. Cl.$^5$ .............................................. C12N 5/08
[52] U.S. Cl. .............................. 435/240.2; 424/93 R; 424/93 B; 424/534; 435/70.5; 435/69.5
[58] Field of Search ................... 435/69.1, 69.5–69.52, 435/240.2; 424/534, 93 A, 93 O, 93 V

[56] References Cited

U.S. PATENT DOCUMENTS 5,166,059 11/1992 Pastan et al. ...................... 435/69.7

OTHER PUBLICATIONS

Kaufmann, Y., et al. (1987) J. Immunol. 139:977–82.
Karasuyama, H. et al. (1989) J. Exp. Med. 169:13–25.
Rosenberg, S. A., et al. (1985) New Engl. J. Med. 313:1485–92.
Nishihara, K., et al. (1988) Cancer Res. 48:4730–35.
Kasid, A., et al. (1990) Proc. Natl. Acad. Sci. USA 87:473–77.
S. H. Chan et al, J. Immunol., 148:92–98 (1992).
D. Santoli et al, J. Immunol., 144(12):4703–4711 (1990).
R. O'Connor et al, J. Immunol., 145(11):3779–3787 (1990).
R. O'Connor et al, Blood, 77(7):1534–1545 (1991).
A. Cesano et al, Blood, 77(11):2463 $\propto$ 2474 (1991).
P. Greenberg et al, J. Biol. Resp. Modifiers, 3(5):455–461 (1984).
J. Klarnet et al, J. Immunol., 142:2187–2191 (1989).
M. Cheever et al, Immunobiol., 172:365–382 (1986).
"First AIDS Gene-Transfer Clinical Comes Before RAC", Biotechnology Newswatch, 11(22)1–3 (Nov. 18, 1991).
"RAC Phases Out Human Gene Therapy Unit; Approves Six New Protocols", Biotechnology Newswatch, 12(4):9–10 (Feb. 17, 1992).
A. Cesano et al, *Oncogene*, 7:826–836 (1992).

Primary Examiner—Garnette D. Draper
Assistant Examiner—David L. Fitzgerald
Attorney, Agent, or Firm—Howson and Howson

[57] ABSTRACT

The invention provides cytotoxic T-ALL cell lines, and modified cytotoxic T-ALL cell lines which contain a heterologous DNA sequence. The DNA sequence may encode a product capable of stabilizing or potentiating the tumoricidal activity of the cytotoxic cell lines and a product capable of controlling the growth of the cell line. Methods for use of these cell lines are also provided.

1 Claim, 2 Drawing Sheets

CYTOTOXIC T-ALL CELL LINES AND USES THEREFOR

This invention has been made with the financial assistance of Grant CA-47589 from the National Institutes of Health. The United States government has certain rights in this invention.

FIELD OF THE INVENTION

This invention relates generally to genetically modified cytotoxic T lymphoblastic leukemia cell lines (T-ALL), and uses of these cell lines in cancer therapy.

BACKGROUND OF THE INVENTION

Within the past ten years, a new therapeutic regimen, called LAK therapy, has been designed for the treatment of solid tumors. According to LAK therapy, a particular population of the patient's own peripheral blood lymphocytes are activated in vitro with IL-2, hence the name "lymphokine activated killer cells" or "LAK" cells. These LAK cells kill tumor cells, while remaining substantially non-toxic to normal cells [E. Grimm et al, *J. Exp. Med.*, 144:1823 (1982); S. Rosenberg, *J. Natl. Can. Inst.*, 75:595 (1985)]. In the presence of recombinant IL-2 in vivo, LAK cells are capable of inducing the regression of established metastatic tumors in animal models [M. Rosenstein et al, *Cancer Res.*, 44: 1946 (1984); J. J. Mule et al, *Science*, 255:1487 (1984); R. Lafreniere et al, *Cancer Res.*, 45:3735 (1985); A. Mazumder et al, *J. Exp. Med.*, 159:495 (1984)]. Promising results have, thereafter, been reported in the management of patients with advanced solid tumors, especially renal carcinoma and melanoma, employing an immunotherapeutic approach with LAK cells and recombinant IL-2, or with IL-2 alone [S. A. Rosenberg et al, *New Engl. J. Med.*, 313: 1485 (1985); S. A. Rosenberg et al, *New Engl. J. Med.*, 316:889 (1987); W. H. West et al, *New Engl. J. Med.*, 316:898 (1987)].

Recent investigations on the use of IL-2/LAK cell therapy in leukemic patients indicate that in patients with a limited proportion of detectable residual blasts, this therapeutic approach may result in the disappearance of the leukemic population [D. Gottlieb et al, *Brit. J. Cancer*, 60:610 (1989)]. However, the same therapy is not successful in patients with advanced disease (90% blasts in the bone marrow) and is associated with significant toxicity as also observed in solid tumor patients [S. Rosenberg et al, *New Engl. J. Med.*, 313: 1485 (1985); S. A. Rosenberg et al, *New Engl. J. Med.*, 316:889 (1987)].

Conventional LAK therapy has several disadvantages. The patient's modified T cells need continuous activation with IL-2 for growth and cytotoxicity. Thus, the process of continuing LAK therapy involves periodic removal and activation in vitro of the patients' normal T cells. Additionally, at the high levels used in LAK therapy, IL-2 is toxic to the patient. The activated T cells are not very cytotoxic and the number of LAK cells that can be produced in vitro and injected in vivo is by necessity limited to a few billion. Few tumors seem to respond to this type of therapy. Thus, while LAK therapy is an improvement over conventional chemotherapy, it is not an optimal therapy for cancer patients.

Analysis of the growth factor requirements and differentiative potential of acute T lymphoblastic leukemias (T-ALL) in children have led to the establishment and characterization of several cell lines bearing the t(8;14) or t(11;14) chromosomal translocations [O'Connor et al, *J. Immunol.*, 145:3779–3787 (1990); and O'Connor et al, *Blood*, 77:1534–1545 (1991) (see Table I)]. Cells from more mature T-ALL cases displayed lymphoid commitment regardless of the growth factor in which they were expanded. In contrast, cells from a very immature T-ALL underwent growth factor-dependent phenotypic conversion (lymphoid to myeloid) when cultured in interleukin (IL)-3 and could be reverted to the T-lineage by switching to growth in IL-2 (see, e.g., Table I below). These cells became established as a continuous cell line designated TALL-103/2 [Santoli et al, *J. Immunol.*, 144(12):4703–4711 (1990) and O'Connor et al, *J. Immunol.*, 145:3779–3787 (1990)].

TALL-103/2 cells are IL-2-dependent and produce high levels of IFN-$\gamma$, TNF-$\alpha$, IL-8 and GM-CSF upon induction with susceptible tumor cells, IL-2 and monoclonal antibodies (mAbs) specific to CD3 and CD2 antigens. This cell line (CD3+ TCR$\gamma\delta$+) is also endowed with non-MHC-restricted cytotoxic activity against those human tumor cells, including leukemias, which are sensitive to Natural Killer (NK) cells [Santoli et al, *J. Immunol.*, 144(12):4703–4711 (1990)]. The stable expression of cytotoxic function over time in culture renders this cell line useful for studies on the mechanism and regulation of lymphocyte-mediated lysis, both in vitro and in vivo. Although IL-2 is required by the cell line for growth and expression of tumoricidal activity, a number of lymphokines, such as IL-4, IL-6, IL-7, IL-12, and interferon (IFN)-$\gamma$ synergize with IL-2 in the induction of cytotoxic activity [Santoli et al, *J. Immunol.*, 144(12):4703–4711 (1990)].

There remains a need in the art for therapeutic methods and compositions thereof for cancers which can utilize cytotoxic T cell lines and avoid the present need in conventional LAK therapy for patient's own killer cells, and which can target selected organs (e.g., brain, liver, lung) which are the sites of metastases.

SUMMARY OF THE INVENTION

In one aspect, the invention provides two novel established leukemia T cell lines, designated TALL-104 and TALL-107. These cell lines are IL-2-dependent and are characterized by the ability to produce high levels of IFN-$\gamma$, TNF-$\alpha$, and GM-CSF upon induction with susceptible tumor cells, IL-2 and/or IL-12, and mAb specific to CD3 and CD2 antigens. These cells are also characterized by cytotoxic activity. TALL-104 and TALL-107 cells display a higher cytotoxic efficiency as compared to TALL-103/2 cells and to LAK cells from normal donors. In addition, they can lyse both NK-sensitive and resistant tumor cells. Further, the cell lines are functionally more efficient than conventional LAK cells for their broad range of tumor reactivity and high killing efficiency (FIG. 1).

In another aspect the present invention provides human cytotoxic T-ALL cell lines or cell lines derived therefrom which are genetically modified to confer one or more of the following characteristics:

(1) controllable growth and survival of T-ALL cell lines in vivo;

(2) elimination from the surface of the cells of those molecules that would cause an immunological rejection of such cells when injected into a host bearing different MHC antigens;

(3) a disposition to favor the targeting of the T-ALL cells to specific organ sites or tumor types; and (4) enhanced or potentiated cytotoxic activity.

As one embodiment of characteristic (1), the invention provides a T-ALL cell into which is inserted a Herpes Simplex Virus-thymidine kinase (HSV-TK) gene or other toxic gene under the regulatory control of an inducible promoter. An embodiment of characteristic (2) is a T-ALL cell line which has been modified by the use of anti-sense technology to eliminate selected MHC molecules from the cell surface. An embodiment of characteristic (3) of the present invention is a T-ALL cell line which has been induced to express on its surface adhesion molecules which would favor its targeting to selected tumors or organs.

An embodiment of the present invention, characteristic (4), is a modified T-ALL cell capable of expressing a lymphokine gene, e.g., IL-2, IL-12, tumor necrosis factor (TNF), IFN, IL-7 and IL-4, which modification confers higher and/or steady levels of cytotoxicity.

Another aspect of the present invention includes a method for producing the modified T-ALL cells described above. In one embodiment, this aspect of the invention provides a method of modifying the T-ALL cell lines by inserting a selected gene which imparts the desired characteristic into the cell. For example, the gene encoding HSV-TK, when inserted into the cell, renders the T-ALL cells sensitive to killing by guanosine analogs, such as acyclovir or gancyclovir.

As still a further aspect, the invention provides a method for killing tumor cells in vivo or ex vivo by exposing the tumor cell to the modified cytotoxic T-ALL cells of this invention, and then treating the cytotoxic T-ALL cells with a substance that prevents their further growth or destroys them entirely.

Other aspects and advantages of the present invention are described further in the following detailed description of the preferred embodiments thereof.

DETAILED DESCRIPTION OF THE INVENTION

Figure 1A:
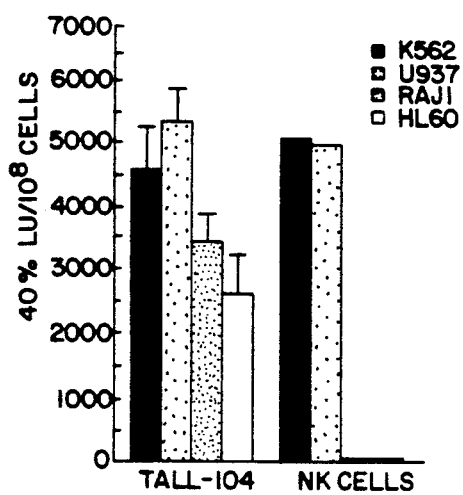
FIG. 1A is a bar graph illustrating the cytotoxic activity of TALL-104 cells as compared to resting NK cells against NK-sensitive K562 and U937 cells and NK-resistant Raji and HL60 target cells.
Figure 1C:
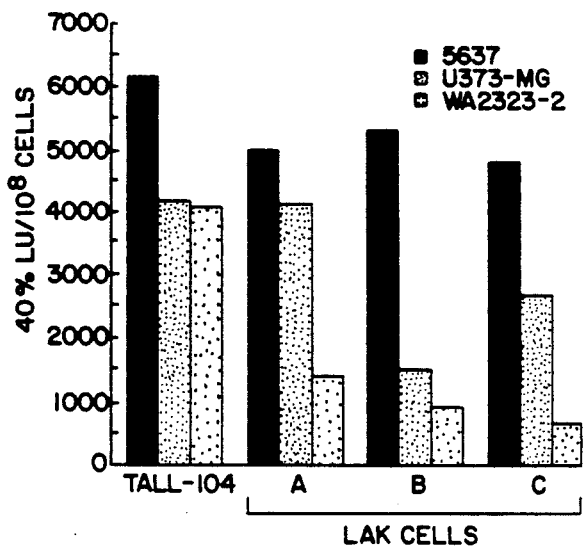
FIG. 1C is a bar graph illustrating the cytotoxicity of TALL-104 cells as compared to normal LAK cells against various targets.
Figure 1B:
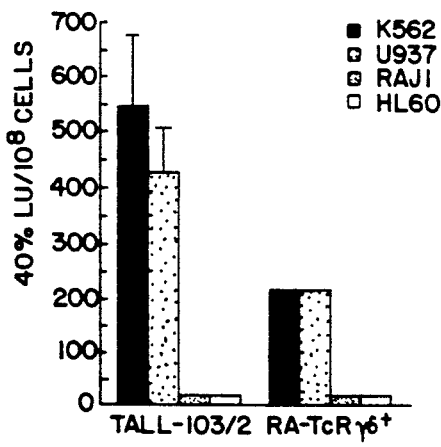
FIG. 1B is a bar graph illustrating the cytotoxic activity of TALL-103/2 cells as compared to IL-2 expanded RA-TCRγδ+ cells against the same target cells.
Figure 1D:
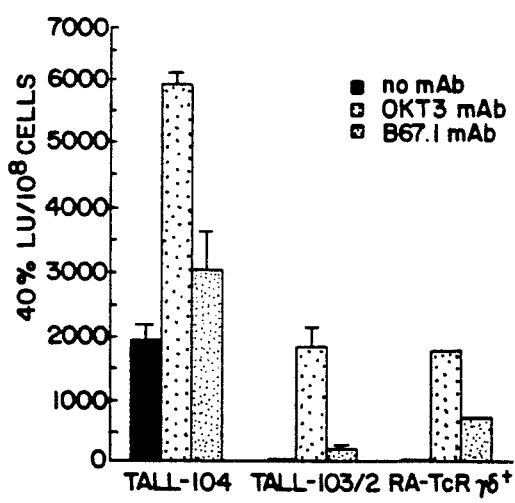
FIG. 1D is a bar graph illustrating the results from four antibody dependent cell cytotoxicity (ADCC) assays in which soluble mAbs were added to TALL-103/2, TALL-104 and RA-TCRγδ+ cells right before adding $^{51}$Cr-labeled FcR+P815 cells.

The present invention provides highly cytotoxic, immortal T cell lines capable of destroying tumor cells in vitro and in vivo. The invention also provides genetically modified cytotoxic T cell lines, the growth of which can be arrested in vivo using a selected agent. These cytotoxic T cell lines and modified cell lines are useful as therapeutics for treating both solid tumors and hematopoietic malignancies. These T-ALL cell lines are also useful in research by providing in vivo models for studying the role of cytotoxic cells in controlling tumor cell growth.

The present invention provides, as one embodiment of a highly cytotoxic T cell line, the cell line TALL-104, an IL-2-dependent T-ALL cell line which expresses high and steady levels of cytotoxic activity against a large spectrum of human tumor cells, including leukemias. This IL-2 dependent TALL-104 cell line is kept within the laboratory of Dr. Daniela Santoli, The Wistar Institute of Anatomy and Biology, Philadelphia, Pa. and may be deposited with an acceptable depository, if necessary. TALL-104 was deposited with the American Type Culture Collection (ATCC), 12301 Parklawn Drive, Rockville, Md. 20852 (U.S.A.), an accepted Depository Authority, on Jun. 15, 1993 and was given the ATCC designation of CRL 11386.

TALL-104 cells express CD3, CD7, CD8, and CD56 antigens and are CD16-. TALL-104 cells are TCRαβ+. These cells mediate non-MHC-restricted cytotoxicity against tumor cells. TALL-104 cells constitutively express low levels of TNF-α, IFN-γ, and granulocytemacrophage colony stimulating factor (GM-CSF) RNA transcripts. The cells can rapidly and efficiently respond to activation signals, such as IL-2, lysable tumor cells and anti-CD3 (OKT3) and/or anti-CD2 (B67.1) monoclonal antibodies by producing high levels of IFN-gamma, TNF-α, and GM-CSF.

Additionally, IL-12 (also known as NKSF) acts as a strong immunopotentiating agent of TALL-104 cells by inducing, independently and synergistically with IL-2 or with OKT-3, both lymphokine secretion (IFN-γ, TNF-α, GM-CSF) and cytotoxic function.

When compared to LAK cells from normal donors, TALL-104 cells display higher killing efficiency against most tumor targets, including the solid tumor cell lines 5637 (bladder carcinoma), U373-MG (glioblastoma) and WA2323-2 (astrocytoma). TALL-104 cells induce two different mechanisms of lysis in two different target cells, apoptosis (internal disintegration or induced suicide) in Raji cells and osmotic death in K562 cells. Necrotic changes in K562 cells by TALL-104 are similar to those induced by conventional NK cells.

TALL-104 cells display an aggressive pattern of growth in vivo infiltrating the tissues of severe combined immunodeficient (SCID) mice [Cesano et al, *Blood*, 77(11):2463-2474 (1991)]. TALL-104 cells have displayed the ability to induce necrosis in melanomas implanted in the skin tissues of SCID mice, and to remarkably reduce or prevent induction of tumors in SCID mice injected with the U937 myeloid leukemia cell line prolonging significantly their survival.

Propagation of TALL-104 cells recovered from SCID mouse tissues in IL-2 has resulted in the spontaneous expansion of a stable clone which no longer requires IL-2 either for continuous growth or for expression of cytotoxic function. This IL-2 independent clone of TALL-104 is also useful for the same applications. The isolation and maintenance of TALL-104 cells is described in detail in O'Connor et al, *Blood*, 77:1534–1545 (1991), which is incorporated by reference herein.

In another embodiment of this invention, the cell line designated TALL-107 is provided. TALL-107 cells were established from another T-ALL patient by growth in the SCID mouse and subsequently adapted to tissue culture conditions. TALL-107 cells are similar to the TALL-104 cells for (a) IL-2-dependency, (b) high levels of cytotoxicity against a broad range of tumor targets, and (c) lymphokine production in response to biological agents. The difference between TALL-107 and TALL-104 cells is the normal karyotype of TALL-107 cells (see Table I). TALL-107 cells are kept within the laboratory of Dr. Daniela Santoli, The Wistar Institute of Anatomy and Biology, Philadelphia, Pa. and may be deposited with an acceptable depository, if necessary.

These cell lines, and the previously described cell line, TALL-103/2 [Santoli et al, *J. Immunol.*, 144(12):4703–4711 (1990); and O'Connor et al, *Blood*, 77:1534–1545 (1991), both incorporated by reference herein], are unique in their ability to produce high levels of tumoricidal lymphokines (IFN-γ and TNF-α) upon induction with several biological agents (IL-2, NKSF/IL-12, tumor cells, anti-CD3 and anti-CD2 monoclonal antibodies). These cell lines also maintain cytotoxic function in vitro upon incubation in IL-2. Thus these cells lines are characterized both by lytic activity and lymphokine production.

The novel cell lines, TALL-104 and TALL-107, are similar to TALL-103/2, in that they are malignant cells that grow without control. In each case, the malignancy of these cells is associated with specific chromosomal translocations or oncogenes, and is not related to transforming viruses. Thus, the cell lines of this invention are further characterized by being free of any contaminating virus, particularly Epstein Barr Virus (EBV) and human retroviruses such as HTLV-I, HTLV-II and Human Immunodeficiency Virus (HIV) as tested by electron microscopy, reverse transcriptase activity, and using specific DNA probes.

These cells offer the advantages over conventional LAK cells of being permanently and rapidly growing in culture in the presence of IL-2, thus being readily available in large quantities, and being phenotypically and functionally stable, thus eliminating the reproducibility problems often encountered with LAK cells from different donors. TALL-104 and the other cytotoxic cell lines of the invention are useful in adoptive transfer immunotherapy against human tumors which are able to grow and metastasize in the mice.

The characteristics of TALL-104 and TALL-107 of this invention, in comparison to other T-ALL cell lines, are summarized in Table I below.

example, Sambrook et al, "Molecular Cloning. A Laboratory Manual", 2nd Edit., Cold Spring Harbor Laboratory, Cold Spring Harbor, N.Y. (1989).

The preferred cytotoxic T cell lines which may be modified according to this invention are acute T lymphoblastic leukemia (T-ALL) cell lines or progeny thereof. Presently, the preferred T-ALL cell lines for modification are TALL-107, TALL-104 and TALL-103/2. Other isolated cytotoxic T cell lines sharing the characteristics of TALL-104, TALL-103/2, and TALL-107, as they are discovered, may also be useful in the compositions and methods of this invention. These T-ALL cell lines may be further modified to extend their range of target selectivity by introducing other cytotoxicity-inducing genes.

A selected T-ALL cell may be modified to incorporate a single desired characteristic. Preferably, a cell line may be modified to incorporate more than one of the characteristics described below. Among desirable characteristics imparted to a T-ALL cell line according to this invention is the characteristic of controllable growth and survival of T-ALL cell lines in vivo. Another characteristic which can be genetically engineered into the selected T-ALL cell line is the elimination from the surface of the cells of those molecules that would cause an immunological rejection of such cells when injected into a host bearing different MHC antigens. Still another desirable characteristic of a modified T-ALL cell line of this invention is a disposition to favor the targeting of the T-ALL cells to specific organ sites or tumor types. A further characteristic which may be imparted to a T-ALL cell line of this invention includes enhanced or potentiated cytotoxic activity.

A selected cytotoxic T-ALL cell line, preferably TALL-104, TALL-103/2 or TALL-107, is modified by inserting into the cell line a gene that provides the desired characteristic, e.g., a mechanism to control the unrestrained growth of the malignant cell. Preferably, amplified copy numbers of the desired gene are inserted into the T-ALL cell line to avoid escape of the inserted gene by mutation.

One example of the above modifications can occur by transfecting the selected T-ALL cell line with a plasmid

TABLE I

| | Chromosomal translocation | Growth factor-dependency | Phenotype | TCR rearrangements | Cytotoxic function | Lymphokine production/gene expression |
|---|---|---|---|---|---|---|
| TALL-101 | t (8;14) | GM-CSF, IL-3, IL-5 | myeloid | β, γ, δ | No | No |
| TALL-103/3 | t (8;14) | IL-3, GM-CSF, IL-5 | myeloid | γ, δ | No | No |
| TALL-103/2 | t (8;14) | IL-2 | lymphoid (T) TCR-γδ+ | γ, δ | Yes | GM-CSF, TNF-α, IFN-γ |
| TALL-104 | t (11;14) (p13; q11) | IL-2 | lymphoid (T) TCR-αβ+ | α, β, γ, δ | Yes | GM-CSF, IFN-γ TNF-α |
| TALL-105 | t (8;14) | none, but grow better in IL-3 | lymphoid (T) TCR-αβ+ | α, β, γ | No | No |
| TALL-106 | t (8;14) | none, but grow better in IL-2 | lymphoid (T) TCR-αβ+ | α, β, γ | No | No |
| TALL-107 | None | IL-2 | lymphoid (T) | α, β, γ | Yes | GM-CSF, IFN-γ, TNF-α |

The present invention also provides genetically modified human cytotoxic T cell lines or cell lines derived therefrom. A selected cytotoxic T cell line of this invention may be modified according to this invention by resort to a variety of conventional recombinant genetic engineering techniques to confer other characteristics to the cell line to expand its research and therapeutic uses. Such techniques are described in standard text, for containing a gene encoding a drug resistance marker rendering the cell sensitive to killing with a selected drug. A gene encoding an enzyme responsive to a certain drug, e.g., a Herpes Simplex Virus thymidine kinase (HSV-TK) gene that will make the cells vulnerable to the toxicity of the guanosine analogs, acyclovir and gancyclovir, may be inserted. Alternatively, other toxic drug markers known to those of skill in the art may be inserted into the T-ALL cell. The details of an exemplary modification of TALL-104 in this manner are disclosed in Example 5, below.

As an example, a toxin gene under an inducible promoter may be introduced into the cell line, e.g., the metallothionein promoter which drives the expression of diphtheria toxin subunit. This subunit will become expressed only when cells are treated with $Zn++$ or $Cd++$. Another modification which is capable of exerting control of the growth of the cytotoxic T-ALL cell line may include inserting into the cell a gene encoding a selected viral antigen that could be recognized by a cytolytic antibody (e.g., rabies glycoprotein recognized by a selected antibody, or influenza hemagglutinin recognized by a specific antibody).

The T-ALL cell line having a cytotoxic effect for tumor cells may be modified by the addition of a gene encoding a selected viral antigen or a selected surface marker that is recognized by a specific antibody. This modification may be in addition to the modification of a growth controlling mechanism as described above. Thus, after the T-ALL cell line is placed in contact with the tumor cell for a sufficient length of time to destroy it, an antibody which is directed to the viral antigen or surface marker on the modified T-ALL cell and which is capable of "killing" the modified T-ALL cell is introduced to the biological system.

Further modifications of T-ALL cells according to this invention may include stabilizing or enhancing the cytotoxic function of the cell line, such as by incorporating into the cell line a selected lymphokine gene, e.g., IL-2, IFN, IL-4, IL-7, IL-12, or TNF, as well as other such cytotoxic factors. For example, it is desirable for a cell line which is dependent for growth upon a particular growth factor to be modified to contain both the gene encoding that growth factor and a sequence encoding a cell growth control mechanism, as described above. The permanent presence of IL-2 in a IL-2 dependent cell line permits the cells to maintain a steady and high level of cytotoxicity [See, e.g., R. Devos et al, *Nucl. Acids Res.*, 11(13):4307–4323 (1983) (which identifies a recombinant plasmid containing human IL-2 cDNA); J. Talmadge, *J. Biol. Resp. Modifiers*, 4:18–34 (1985) (rhIL-2 augments NK cell activity in vitro and in vivo and T cell activity in vitro); see also, L. Lanier et al, *J. Exp. Med.*, 167:1572–1585 (1988)]. Preferably, the insertion of the IL-2 gene into the T-ALL cells induces the production of IL-2 in amounts that are sufficient to maintain the cells, but are not toxic to any patient to whom the modified cells are administered.

Another example is a mutant TNF cDNA molecule [Perez et al, *Cell*, 63:251 (1990)] which may be introduced into the LTR region of a retroviral vector for transfection into the selected T-ALL cell line. This TNF lacks a protease cleavage site in its extracellular domain, remains bound to the cells that are producing it, and confers increased cytotoxic activity to the cells that carry it on their surface. As described in Perez et al, cited above, this TNF sequence may be prepared by site directed mutagenesis using available TNF cDNA.

Another modification of a T-ALL cell line according to this invention involves extending the cell line's range of target selectivity or increasing the cell's ability to favor the targeting of specific organ sites or tumor sites. This modification may be accomplished, for example, by inducing surface expression of adhesion molecules or lymphocyte homing receptors. One example of an organ specific adhesion molecule is Lu-ECAM-1, which is lung specific [D. Zhu et al, *Proc. Natl. Acad. Sci., USA*, 88:9568–9572 (1991)]. The $\beta$-3 integrin subunit which is expressed only by metastatic and vertical growth phase melanomas is an example of cell-adhesion molecules associated with tumors [S. M. Albelda et al, *Cancer Research*, 58:6757–6764 (1990)]. Another such example is the carcinoembryonic antigen (CEA) which is associated with colon carcinoma and other tumors [S. Benchimol et al, *Cell*, 57:327–334 (1989)]. Among the molecules mediating lymphocyte-endothelial cell adhesion and lymphocyte migration into the surrounding tissues are the selectins, integrins, immunoglobulin supergene family molecules, CD44, and T-lineage molecules such as CD4, CD8, etc [reviews by C. A. Buck, *Cell. Biol.*, 3, in press, (1992), E. C. Butcher, *Am. J. Pathol.*, 136:3–11 (1990), and Y. Shimizu et al, *Immunology Today*, 13:106–112 (1992)].

Alternatively, a T-ALL cell of this invention may have its targeting ability for specific tumors increased by the use of bivalent antibodies against a selected tumor antigen. For example, antibodies against epidermal growth factor receptor (EGFR), optionally coupled to the T-ALL cell or administered concurrently therewith, may target the T-ALL cell to gliomas, melanomas and also to liver. Such a construct may be employed in a therapeutic composition.

Still another modification of the TALL cells of this invention involves the elimination from the surface of the cell of those molecules that would induce a graft versus host disease, or rejection, in the patient. This may be done applying to the T-ALL cells of this invention the anti-sense technology against the major histocompatibility complex (MHC) molecules, as described in R. K. Groger et al, *Gene*, 81:285–294 (1989), incorporated herein by reference.

The modified cell lines of the invention having one, and preferably more than one, of the characteristics described above, provide advantages over the T cells presently used in LAK therapy. The modified cytotoxic T-ALL cells of this invention can eliminate the need for producing killer cells from individual patients. These modified cells can also kill tumor cells very efficiently (see, e.g., FIG. 1, Example 3). In addition, these T-ALL cells can be rapidly expanded both in vitro and in vivo in an immunodeficient host, e.g., a SCID mouse, thus being promptly available in large quantity.

In order to modify the selected T-ALL cell lines in any of the selected ways described above, one of skill in the art may select any conventional vector or plasmid capable of introducing a heterologous sequence into the cell line. The introduced gene may be extrachromosomal. Alternatively it may be inserted into the cell's chromosomes. It is presently preferred that retroviral vectors be employed because of their efficiency in transfecting cells. However, any other type of suitable vector can be used. Numerous such vectors are known and available to the art.

As an example, the following retroviral vectors may be used to modify a T-ALL cell of this invention, e.g., to permanently insert an IL-2 gene into a T-ALL, IL-2 dependent cell line. One suitable retroviral vector DC/IL-2 contains the human IL-2 cDNA driven by the TK promoter and is described in B. Gansbacher et al, *J. Exp. Med.*, 172:1217 (1990). This vector has been modified by inserting at the 3' end of the neo gene, an HSV-TK gene driven by its own promoter and containing its own polyA addition site. Two constructs were made to contain the HSV-TK in a forward and reverse orientation. These constructs have been used to generate an amphotropic retrovirus using the AM12 packaging line [Markowitz et al, *Virol.*, 167:400 (1988)]. This recombinant virus is used to infect the T-ALL cells using the methods described in Markowitz et al, *J. Virol.*, 62:1120 (1988), and to transfect the vector directly into T-ALL cells.

Another retroviral vector which may be used is N2A, which was obtained from Dr. Gilboa at Memorial Sloan-Kettering Cancer Center, and is described in Hantzopoulos et al, *Proc. Natl. Acad. Sci. USA*, 86:3519 (1989) and Armentano et al, *J. Virol.*, 61:1647 (1987). This vector has a polylinker site instead of a neo gene and is particularly useful for introducing HSV-TK or other drug resistance markers into the vector polylinker site.

The recombinant retroviral vector carrying the modification gene(s) infects the T-ALL cells using published methods [See, for example, Markowitz et al, *Virol.*, 167:400 (1988) and Markowitz et al, *J. Virol.*, 62:1120 (1988)].

Optionally, after modification of the selected cells to contain a drug resistance marker, the cells may then be further modified by inserting other desired DNA sequences, e.g., additional markers, regulatory genes, or targeting genes, in the LTR region in order to express the genes in double copy (DC) vectors [Armentano et al, *J. Virol.*, 61:1647 (1987)].

Alternatively, the IL-2 cDNA or other desired gene or sequence may be cloned into a known plasmid vector, of which a variety are conventionally used to insert heterologous DNA into mammalian cells. In the practice of this invention, the desired heterologous polynucleotide sequence may be cloned into a conventional expression vector or plasmid, for example, a pXM expression vector [Y. C. Yang et al, *Cell*, 47:3–10 (1986)] or a pBC12 vector [B. Cullen, *Cell*, 46:973 (1986)] for transfection by known means into the cell line.

Any conventional plasmid vector suitable for expression into mammalian cells may be used for this purpose. The selection of a suitable vector is conventional to one of skill in the art, and this invention is not limited by the nature of the vector selected.

The cloning techniques used to construct the vectors and transform the T-ALL cells are standard and known to one of skill in the art [see, e.g., Sambrook et al, cited above]. When plasmids are used, the T-ALL cells can be transfected using either electroporation or, preferably, lipofection techniques. Traditional techniques of calcium phosphate or the DEAE-dextran may also be used. These and other known techniques of expressing transfected DNA may be used in the present invention.

Electroporation can be accomplished by using the BIO-RAD® Gene Pulser. This technique involves electroporating the cells by delivering an electric pulse to a suspension containing the T-ALL cells and linearized plasmid DNA. This pulsing permits disruptions in the cell membrane large enough to permit entry of the plasmid DNA; after the pulsing is stopped, the cell membranes are not disrupted.

The technique of lipofection is described by Felgner et al, *Proc. Natl. Acad. Sci. USA*, 84:7413 (1987). This technique involves mixing plasmid DNA with LIPO-FECTIN (TM,Gibro/BRL) and incubating the cells with the mixture. Currently, lipofection is preferred over electroporation because it appears to be more effective in generating stable transfectants. Additionally, lipofection is preferred to the known calcium phosphate or the DEAE-dextran methods for stable expression of transfected DNA because it has been reported to be considerably more effective than either of those methods. This method is described in more detail in Example 5 below.

As described in the following examples, the cell lines and modified cell lines of this invention have a variety of uses in both therapy and research. The cell lines may be used in a therapeutic regimen in the treatment of cancers. When intended for use in animals, particularly humans, the cytotoxic cell lines and modified cell lines of the present invention are first tested for tumoricidal activity and therapeutic efficacy in animal models, preferably the SCID mouse described in Cesano et al, *Blood*, 77:2463–2474 (1991), incorporated herein by reference. Such studies in mice are necessary preclinical studies performed before patient therapy is undertaken.

This invention thus provides a method of treating human cancers, including leukemias, by administering to a patient an effective tumoricidal amount of a modified cytotoxic T-ALL cell line, preferably TALL-104, TALL-107 or TALL-103/2, which has been transfected with a drug resistance gene, e.g., HSV-TK, for a time sufficient for the modified T-ALL cells to kill the patient's tumor cells. The T-ALL cells are thereafter killed by exposing them to the selected drug. For the HSV-TK gene, the drug is a guanosine analog, such as acyclovir or gancyclovir.

This method of the invention may be performed either in vivo or ex vivo, depending on the type of cancer to be treated. When the cancer is a hematopoietic tumor, the method may be performed ex vivo in a manner similar to bone marrow purging, in which the patient's cells are withdrawn and exposed to the modified cytotoxic T-ALL cells outside of the body. After a sufficient time for the modified T-ALL cells to kill the target leukemia cells outside of the body, the cells are treated with the appropriate drug which is capable of killing the modified T-ALL cells containing the drug-sensitive gene. The patient's cells may then be separated from the modified T-ALL cells and returned to the patient.

However, it is preferred that the method of this invention be performed in vivo by administering directly to the patient the modified cytotoxic T cell line. In vivo application of this method permits the treatment of all cancers, including those characterized by solid tumors. The transfected modified T-ALL cells would desirably be present in a conventional pharmaceutical excipient, such as water or buffered saline. Upon administration to the patient, the modified cells can arrest the growth of tumor cells by means of tumor-directed killing. For human patients, the T-ALL cells may be injected intravenously (i.v.). However, other methods of administration, such as subcutaneous (s.c.) injection may be utilized. Upon successful eradication of the neoplastic cells, which can be determined by the methods described below, the T-ALL/drug resistance gene killer cells are eliminated by administration of non-toxic doses of the appropriate drug.

The use of HSV-TK as the drug resistance gene (preferably amplified or at least in double copy) in the modified T-ALL cells is preferred because the acyclovir and gancyclovir drugs to which the gene is sensitive are presently routinely used in vivo as therapy for HSV infections and their level of toxicity is very low. Preferably, the acyclovir [Wellcome-Burroughs, Charlotte, N.C.] or gancyclovir [Syntex Research, Palo Alto, Calif.] is administered to a patient who has been treated with the transfected T-ALL cells of the invention by injection of between about 1 to about 50 mg drug/kg body weight/day. The administration of these drugs (or any other drug appropriate to the marker used) is not limited to these routes of administration, dosages, or frequency of administration. Other appropriate routes of administration and duration or repetition or treatment may be selected by the attending physician.

Appropriate dosages of the modified cells and the drug vary depending upon the age, health, sex, and weight of the recipient, as well as any other concurrent treatments the recipient is undergoing for related or non-related conditions, and the specific T-ALL cell line which is being used. One of skill in the art can readily determine the appropriate dose of the modified cells and drug to be administered to the patient, depending on factors including the mode of treatment, e.g., in vivo or ex vivo, and the type of cancer to be treated. The number of cells that constitute an effective tumoricidal amount can be determined using animal models. These parameters can be readily determined by one of skill in the art.

Once the modified T-ALL cells are killed with the appropriate drug, the body's naturally functioning immune system removes the killed modified T-ALL cells. In one embodiment, a patient may be immunosuppressed using conventional drugs before and during the administration of the therapeutic method of the invention. Following administration of the modified T-ALL cells and the drug, e.g, acyclovir, the immunosuppressive therapy would be discontinued.

The therapeutic method of the invention is particularly advantageous because, in contrast to LAK therapies which require "customizing" the cells of the individual being treated, the method of the present invention provides a "universal" cell which is independent of the patient's cells. For example, a modified TALL-104TK+ cell would be used in therapy, and therefore no additional invasive procedures would be involved, such as removing the patient's own cells for modification. The invention therefore also reduces the cost of such treatment. Further, this method of the invention utilizes cells, which can be permanently cultured in the presence of IL-2, maintaining both tumoricidal activity and ability to release cytotoxic lymphokines. In contrast, conventional LAK therapy involves the use of normal T cells which have a life span of only a few weeks.

The effectiveness of this therapy against leukemia may be determined by detection of any surviving leukemic cells in samples of the patient's peripheral blood cells (PBC) or bone marrow. Detection and quantitation of residual leukemic cells in vivo may preferably be performed by polymerase chain reaction (PCR) amplification of rearranged immunoglobulin or T-cell receptor gene sequences using VDJ joining specific oligonucleotides probes. Similarly, any residual, unwanted modified T-ALL cells may be monitored using the same methods for detection of minimal residual disease.

Synthetic oligonucleotide primers and leukemia-specific probes are synthesized according to known techniques [M. Yamada et al, Proc. Natl. Acad. Sci. USA, 86:5123 (1989)]. Probes specific to each ALL may be used to detect residual leukemic cells also by using in situ hybridization techniques. Briefly, recombinant plasmids containing the sequences of interest are linearized using the appropriate restriction enzymes and transcribed into antisense (positive) and sense (negative control) RNA probes, such as by use of $^{35}S$-UTP [NEN, DuPont Co., Wilmington, Del.] and the PROMEGA ® Riboprobe Kit [Promega Biotec, Madison, Wis.]. Patient PBC or bone marrow are fixed on slides and exposed to the probes. The slides are then evaluated at $400\times$ and $1000\times$ magnification by screening fields at low and high magnification and counting positive cells.

To evaluate therapeutic efficacy in solid tumor patients, immunohistochemistry techniques can be applied to biopsy specimens. Also techniques such as, magnetic resonance imaging (MRI), or radioactive markers may be used by physicians.

The following examples illustrate the preferred methods for preparing modified cell lines of the invention. Examples 1 and 2 detail the development of the TALL-104 cell lines. Example 3 describes the cytotoxic characteristics of these cell lines in various assays. Example 4 describes the genetic modification of TALL-104 cell line by the insertion of an HSV TK gene, which is useful to control growth of the cell. Example 5 describes the study of the modified T-ALL cell of this invention in an animal model. Example 6 describes the construction of probes to detect the modified cells and monitor the treatment in an animal patient. Example 7 describes the quantitation of residual leukemic cells. These examples are illustrative only and do not limit the scope of the invention.

EXAMPLE 1—IL-2 DEPENDENT TALL-104 CELL LINE

The origin and establishment of the IL-2-dependent TALL-104 cell line from the peripheral blood of a T-ALL patient, case CH-23, is described in O'Connor et al, Blood, 77:1534–1545 (1991), incorporated by reference herein. Briefly, mononuclear cells from the leukemic samples were separated by Ficoll Hypaque gradient centrifugation and plated in 24-well Linbro plates [Flow Laboratory, McLean, Va.] at a concentration of $1\times10^6$/mL in Iscove's modified Dulbecco's medium (IMDM) [Gibco, Grand Island, N.Y.] supplemented with 10% fetal bovine serum [Hycone, Logan, Utah] and antibiotics (complete medium). Recombinant human (rh) preparations of growth factors IL-2, GM-CSF and IL-3 were added at specific concentrations.

The cells initially proliferated in the presence of IL-2 [Amgen], IL-3 and GM-CSF [Genetics Institute] and in the absence of added growth factors. However, after two months in culture, it became apparent that the cells in IL-2 proliferated much faster than those in the other conditions. These cells became established as an IL-2-dependent cell line, designated TALL-104, whereas those maintained in IL-3, GM-CSF, or no factor had a finite life span of about 6 months.

This TALL-104 cell line has been in continuous culture for two years in the laboratories of Dr. Santoli. The TALL-104 cells are maintained at 37° C. in 7% $CO_2$ in IMDM (Gibco) supplemented with 10% fetal bovine serum. Biweekly addition of fresh medium containing rhIL-2 is required for optimal viability and continuous growth of TALL-104 cells, but these cells can also be propagated, at a slower rate, in the absence of this factor for a few weeks and lose cytotoxic activity gradually.

EXAMPLE 2—IL-2 INDEPENDENT TALL-104 CELL LINE

TALL-104 cells (see Example 1) were engrafted into severe combined immune-deficient (SCID) mice leading to aggressive and fatal disease [Cesano et al, *Blood*, 77:2463-2474 (1991)]. Upon recovery from SCID mouse tissues and culture in rh IL-2, a clone of TALL-104 cells spontaneously arose which had lost the requirement for IL-2 for continuous growth. The growth factor independent clone displayed the same levels of cytotoxic efficiency against NK-sensitive (K562) targets as the parental IL-2 dependent cell line. In contrast, killing of NK-resistant (Raji) targets appears slightly lower in the IL-2 independent cells.

EXAMPLE 3—CYTOTOXICITY OF TALL-104 AND TALL-103/2

A. $^{51}$Cr-release assays

The tumoricidal activity of the IL-2 dependent TALL-104 and TALL-103/2 cell lines has been studied in detail, using standard $^{51}$Cr-release assays, as described [Cesano et al, *Blood*, 77:2463-2474 (1991); Santoli et al, *J. Immunol.*, (1990); and Santoli et al, *Cell Immunol.*, 65:230 (1981)].

Prior to the assay, the effector cells were incubated in 10 U/mL rhIL-2. FIG. 1, panels A to C, are bar graphs illustrating the cytotoxic activity of TALL-104 and TALL-103/2 cells as compared to resting NK cells and IL-2 expanded RA-TCRγδ+ cells against NK-sensitive leukemia K562 and U937 cells and NK-resistant Raji and HL60 target cells.

TALL-104 cells cultured in the IL-2 were found to lyse both NK-sensitive targets (K562 and U937) and NK-resistant tumor cells (Raji and HL60). In contrast, TALL-103/2 cells only lyse NK-susceptible targets.

B. Reverse Antibody Dependent Cell-Mediated Cytotoxicity (ADCC) assay

The possibility of triggering the lytic machinery of the TALL-104 and TALL-103/2 cells lines using monoclonal antibodies (mAb) recognizing specific T cell surface molecules was investigated. Conventional reverse (redirected) ADCC assays were performed against murine IgG Fc-receptor-positive (FcR+) P815 [ATCC #TIB 64] cells by incubating the effector cells in the presence of 10 U/mL IL-2 and mAbs specific for CD2, CD3, CD8 and CD56.

FIG. 1, panel D is a bar graph illustrating the results from four ADCC assays in which soluble mAbs were added to TALL-103/2, TALL-104 and RA-TCRγδ+ cells right before adding $^{51}$Cr-labeled FcR+P815 cells. Four different E:T ratios (50:1, 25:1, 12.5:1 and 6.2:1) were used in each four hour $^{51}$Cr-release assay. Bars represent standard deviations from between three to five experiments.

In the absence of mAb stimulation, P815 cells could be lysed by TALL-104 cells but not TALL-103/2 cells. High levels of cytotoxicity were always induced in TALL-103/2 and TALL-104 cells by stimulation with the anti-CD3 mAb OKT3 [Ortho Pharmaceuticals, Rariton, N.J.]. Triggering of CD2 with B67.1 mAb induced low but reproducible levels of cytotoxicity. P815 cells were not lysed at all if the effectors were treated with mAb specific to CD8 (OKT8) [Ortho Pharmaceuticals] and to CD56 (anti-Leu-19) [Becton Dickinson, Mountain View, Calif]. Additionally, none of these mAb (anti-CD2, -CD8, -CD56) affected the cytotoxicity triggered by OKT3 antibody.

In the reverse ADCC assays, TALL-103/2 cells displayed levels of cytotoxicity four-fold higher than those expressed in conventional NK assays against K562 cells.

C. SCID Mouse Assays

SCID mouse assays were performed as described in Cesano et al, *Blood*, 77:2463-2474 (1991), using TALL-104. Preliminary experiments in the SCID mouse have recently shown that TALL-104 cells can arrest tumor growth and prolong the survival of animals transplanted with a myelomonocytic leukemia (U937).

EXAMPLE 4—MODIFYING CYTOTOXIC CELL LINES

The following example describes the modification of the TALL-104 cell line to contain a drug selectable marker gene, HSV-TK. The same procedures may similarly be used on TALL-103/2 and TALL-107; however, for simplicity, the procedures are described in detail only with reference to TALL-104. One of skill in the art could adapt the method to insert the TK+ marker into other T-ALL cell lines, or to insert other known markers or viral antigens which are expressed on the cell surface into the T-ALL cell lines.

Preferably single copy, double copy (DC) or multiple copy vectors are employed in this method to avoid mutation problems which can render the cells insensitive to HSV-specific drugs.

Figure 2:
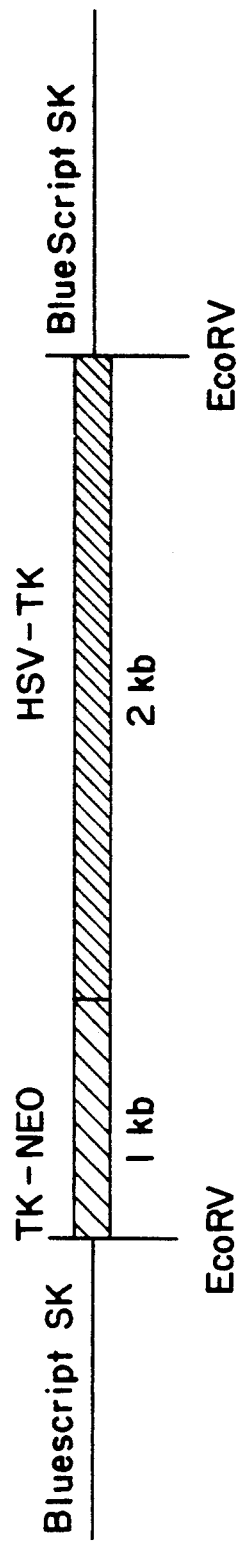
FIG. 2 illustrates a Bluescript (TM, stratagene) plasmid construct containing the HSV-TK gene.

Recombinant Bluescript plasmids are prepared by standard protocols [Sambrook et al, *Molecular Cloning. A Laboratory Manual.* 2d edit., Cold Spring Harbor Laboratory, New York (1989)] to contain the HSV-TK gene and the neo gene for selection of G-418-resistant clones. One construct made in Dr. Rovera's laboratory is in a Bluescript vector in which the Xho-Baml insert of the plasmid pMC1 Neo-polyA and the PvuII 2kb fragment of the plasmid pHSV-106 have been inserted in the EcoRV site (FIG. 2).

The IL-2 dependent TALL-104 cells described in Example 1 were transfected with HSV-TK cDNA using the resulting plasmid. The lipofection method was used for transfection, in which 20 μg linearized plasmid DNA and 30 μg LIPOFECTIN ™ [BRL, Gaithersburg, Md.] (bathed in 50 μL water) are gently mixed and the mixture allowed to stand for 15 minutes at 20° C. Actively dividing TALL-104 cells ($10^7$) are washed twice in serum-free medium and suspended at $1 \times 10^6$/mL in this medium. The lipofectin-DNA complex is then added dropwise to the cell suspension followed by incubation for 24 hours at 37° C. in serum-free medium. Cells are washed and suspended in medium containing 10% FBS and 5 days later selection with the marker G-148 sulfate is initiated, as described below.

Transfection with the TK gene of HSV was done to render the cells sensitive to the DNA synthesis inhibitory effects of the nucleoside analogs, 9-(2-hydroxyethoxymethyl) guanine, which has the generic name "acyclovir" or DHPH-9-(1,3-Dihydroxy-2-propoxy[-methyl]guanine), which has the generic name "gancyclovir". Acyclovir has an inhibitory activity for HSV-1 greater than any presently known compound, and has extremely low cytotoxicity to uninfected cells.

After insertion of the HSV-TK gene, the cells are incubated in IMDM medium with 10% fetal bovine serum (FBS) for 24-48 hours, transferred to 24-well tissue culture plates (2 mL aliquots) and subsequently transferred into selective medium containing ≧1 mg/mL geneticin (G-418 sulfate) [Gibco Laboratories]. These doses of G-418 inhibit approximately 100% the proliferation of non-transfected parental TALL-104 cells in a 7 day culture.

G-418-resistant (HSV-TK) clones are selected and tested in short-term proliferation assays for sensitivity to either acyclovir [Wellcome-Burroughs, Charlotte, N.C.] or gancyclovir [Syntex Research, Palo Alto, Calif.] at concentrations which are non-toxic for normal cells, but highly toxic for HSV-TK transfectants, e.g. about 10-50 μM. In the proliferative assay, the cells are seeded in IMDM at $5 \times 10^4$/well in 96-well microtiter plates [Falcon, Becton Dickinson, Oxnard, Calif.] in the presence and absence of various concentrations of recombinant human IL-2 [Hoffman-LaRoche], GP-418, acyclovir or gancyclovir. After three days, the cells are pulsed with 2 μCi[$^3$H]TdR (2 Ci/mmol) for 6-18 hours and harvested on fiberglass filters by an automated cell harvester [Skatron, Sterling, Va.]. Isotope incorporation is measured with a Beckman liquid scintillation counter.

A number of TK+ transfectants are obtained whose growth is completely inhibited by low concentrations (5-10 μM) of acyclovir. In contrast, the in vitro growth and viability of the parental (nontransfected) TALL-104 cells are completely unaffected by incubation in the presence of acyclovir even at 100 μM.

Acyclovir is toxic to the transfectants because the acyclovir is metabolized into acyclo-GTP. This metabolite is subsequently incorporated in the DNA of the transfected cells, causes induction of DNA chain termination, and cell death results. Resistance of nontransfected cells to acyclovir is due to the fact that these cells do not recognize acyclovir as a nucleoside. After four weeks, the cell are diluted and cloned in agar in the presence of GENETICIN ® brand antibiotic. Transfectants are maintained in 500 μg/mL of drug.

Another modification of a T-ALL cell line according to this invention involves inserting the IL-2 gene into the TALL-104 cells. For this purpose, a DC retroviral vector [Drs. Gilboa and Gansbacher] is used containing the human IL-2 cDNA driven by the TK promoter as described in B. Gansbacher et al (1990), cited above. The vector is modified by inserting an HSV-TK gene driven by its own promoter and containing its own polyA addition site at the 3' end of the neo gene.

Other constructs are made to contain the HSV-TK in a forward and reverse orientation. These constructs are used to generate an amphotropic retrovirus using the AM12 packaging line [Markowitz et al, (1988) and (1988), cited above].

EXAMPLE 5—EFFECT OF MODIFIED TALL-104/TK+ CELLS ON ANIMAL MODEL

The modified T-ALL cells of Example 4 and the methods of this invention are tested in the animal model, the Severe Combined Immunodeficient (SCID) mouse. One group of SCID mice are engrafted with TALL-104/TK+ cells according to the methods described by Cesano et al, Blood, 77:2463-2474 (1991). Another group of SCID mice are injected with non-transfected TALL-104 cells. Both groups of mice are treated with the same doses of guanosine analogs, acyclovir or gancyclovir. Another group of SCID mice engrafted with TALL-104/TK+ cells but left untreated serve as a positive control group.

According to this experiment, mice are injected with various doses of acyclovir (with a maximum of 10 mg/kg/day) at 1, 2, 4, and 6 weeks after TALL-104/TK+ transfer, and daily thereafter. Blood samples are taken from the tail vein of the mice at weekly intervals to monitor treatment efficacy. Some mice are sacrificed and examined for gross pathology (tumor mass, large thymus, and splenomegaly) and microscopic appearance of tissues. Other mice are kept alive for several months in order to monitor the possible induction of a much slower disease induced by the acyclovir-escaped cells.

If, after treatment, surviving TALL-104/TK+ cells cannot be microscopically detected in the mouse tissues, their presence is analyzed by the PCR amplification of TCR rearrangements sequences. TALL-104 cells display TCR rearrangements of $\alpha$, $\beta$, $\gamma$, and $\delta$ genes (see Table I).

Preferably, the method described by Hansen-Hagge et al, Blood, 74:1762 (1989) for amplification of rearranged sequenced TCR-δ chain sequences is used, because, in contrast to methods proceeding from amplified TCRγ sequences, this method does not require sequence analysis of the junctional regions and synthesis of leukemia-specific oligonucleotide probes.

Alternatively, probes specific to each ALL are used to detect residual leukemic cells by using in situ hybridization techniques. Recombinant Bluescript plasmids, prepared by standard protocols [Sambrook et al, Molecular Cloning. A Laboratory Manual. 2d edit., Cold Spring Harbor Laboratory, New York (1989)], containing the sequences of interest are linearized using the appropriate restriction enzymes and transcribed into antisense (positive) and sense (negative control) RNA probes using $^{35}$S-UTP [NEN, DuPont Co., Wilmington, Del.] and the PROMEGA ® Riboprobe Kit [Promega Biotec, Madison, Wis.] according to the manufacturer's instructions with the following modifications. After transcription and ethanol precipitation, the probe is resuspended in 50 μL of 20 mM DTT in diethyl pyrocarbonate (DEPC)-H$_2$O. Fifty μL of carbonate buffer, pH 10.2 (80 mM NaHCO$_3$ and 120 mM Na$_2$CO$_3$) is added, and a limited alkaline hydrolysis is carried out by incubation for 30 minutes at 60° C.

Probes are then neutralized by the addition of 5 μL 10% acetic acid and ethanol precipitated [L. Angerer, "In situ hybridization with RNA probes, and annotated recipe", in Applications to Neurobiology, Oxford University Press, Oxford UK (1986)]. For each experimental condition, 5 to $10 \times 10^6$ cells (from blood, marrow, spleen, liver, and other tissues) are centrifuged over a Ficoll/Hypaque gradient [Lymphoprep, Nygaard and Co., Oslo, Norway], washed, and resuspended in 5 mL RPMI-1640 with 10% FBS. One hundred to 200 μL of cell suspension is cytospun onto organosilane treated slides using a cyto-centrifuge. Slides are dried 5 minutes, fixed in 4% paraformaldehyde-PBS for 15 minutes, washed 3× in PBS for 3 minutes each, dehydrated through graded ethanols, air-dried, and stored with desiccant at −70° C.

Pretreatment of slides and hybridization with $^{35}$S-labeled riboprobes is carried out at 45° C. overnight, as described by Halpern et al, Cont. Clin. Trials, 8:177 (1987). After removal of coverslips, slides are washed 2× for 10 minutes in 2× SSC on a rocker; 4× in 0.25× SSC, 1 mM EDTA, 1 mM DTT for 15 minutes in a shaking water bath at 55° C. Unhybridized RNA probe is digested by incubating slides with 40 μg/ml RNAase A [Sigma Chemical Co.] in 10 mM Tris, pH 8.0, 0.3M NaCl for 30 minutes at 37° C. Slides are then washed 2× in 50 formamide, 2× SSC, 1 mM DTT for 30 minutes at 55° C.; and finally, in 2× SSC, 1 mM DTT for 30 minutes at 55° C. After dehydration in graded ethanols containing 0.3M ammonium acetate and air drying, slides are dipped in NTB 3 autoradiography emulsion [Eastman Kodak, Rochester, N.Y.] and diluted 1:1 with 0.6M ammonium acetate in DEPC-$H_2O$.

After exposure for 3 to 7 days at 4° C., slides are developed with KODAK ® brand D-10 developer, fixed with Kodak Rapidfix, and counter stained with hematoxylin and eosin. Slides are then evaluated at 400× and 1000× magnification by screening fields at low and high magnification and counting positive cells. Any detectable cell count indicates a condition requiring further treatment.

EXAMPLE 6—AMPLIFICATION AND SEQUENCING OF THE VDJ JOINING OF ALL CELLS AND PREPARATION OF DIAGNOSTIC PROBES

This example describes the construction of probes to detect residual cells in an animal or human treated with the modified cell lines of this invention. Depending on the leukemia being treated, individual probes are needed. However, one of skill in the art can develop such probes, using this description as a guideline.

High molecular weight DNA from ALL cell lines is isolated using SDS proteina- K digestion [A. Pellicer et al, *Cell*, 14:133 (1978)]. Rearrangements of the IgH gene of the B-ALL cell lines (ALL-1, -2, -3) and of the TCR genes of the TALL-104 and -106 cell lines have been described in B. Lange et al, *Blood*, 70:192 (1987) and Table I above.

PCR is used to selectively amplify the VDJ joining of these cell lines using their DNA as a template. Primers for the B-lineage cell lines is the V(670)Sal and J(36)Pst oligonucleotides [M. Yamada et al, (1989), cited above]. The 5' end of these primers has been modified to allow for the presence of restriction sites suitable for cloning. For example, the TCR-γ rearrangement of TALL-104 cells are PCR amplified using Vγ9 and Jγ oligonucleotides as primers [D'Auriol et al, *Leukemia*, 3:155 (1989)]. The amplification primers Vγ9 and Jγ can also be used for TALL-104 cells. However, oligomers specific for Vδ1 and Vδ1 rearrangements [Hansen-Lagge et al, *Blood*, 74:1762 (1989)] are preferred because the method to amplify rearranged TCR-δ chain sequences does not require sequence analysis of the junctional regions and synthesis of leukemia-specific oligonucleotide probes.

The PCR is carried out as described by Mullis and Faloona, *Methods. Enzymol.*, 55:335 (1987) and Saiki et al, *Science*, 239:487 (1988), using an Ericomp thermal cycler. Briefly, the PCR is performed as follows. The initial denaturation step is at 95° C. for 5 minutes, followed by 30 cycles with a 1 minute annealing step at 55° C., a 2 minute elongation step, and a 2 minute denaturation step at 95° C. The final cycle is completed with a 7 minute elongation step. Precautions against cross-contamination of amplified material are taken according to Kwok et al, "Application of the polymerase chain reaction to the detection of human retroviruses" in *Polymerase Chain Reaction*, ed. H. Erlich et al, Cold Spring Harbor, Cold Spring Harbor Laboratory Press, p. 151 (1989).

After phenol/chloroform extraction and ethanol precipitation, part of the amplified DNA will be digested with suitable restriction enzymes [Boehringer-Mannheim, Indianapolis, Ind.] purified on agarose gels, and subcloned into Bluescript phage [Stratagene, La Jolla, Calif.] as described in Yamada et al, *New Engl. J. Med.*, 323:448 (1990). Recombinant colonies are identified using diagnostic probes nested inside the J primers used for amplification. The sequence of the recombinant plasmids is determined using the double stranded dideoxy sequencing method [F. Sanger et al, *Proc. Natl. Acad. Sci. USA*, 74:5463 (1977)].

Diagnostic probes specific for each leukemic cell line are designed by choosing an area of 20 mer oligonucleotide overlapping the DJ junction [See e.g., Yamada et al, (1989) and (1990), both cited above]. The diagnostic probes generated from these sequences will hybridize only to the amplified IgH or TCR rearrangements from which the sequences are derived and are used to specifically quantitate residual leukemic cells in SCID mouse tissues.

EXAMPLE 7—QUANTITATION OF RESIDUAL LEUKEMIC CELLS IN SCID MOUSE TISSUES

To quantitate the presence of ALL cells in SCID mouse tissues, tissue cells are resuspended and counted. To these cells are added cells from a B or T cell line different from the ALL under study, in an amount equal to one tenth the volume of ALL cells. The mixture is subjected to DNA preparation and the IgH or TCR gene rearrangement sequences of the ALL are amplified by PCR using suitable primers. The amplified VDJ joining regions are cloned into an M13 phage library [Yamada et al, (1990), cited above]. Duplicate nitrocellulose filters [BA 85, Schleicher and Schuell, Keene, N.H.] containing the recombinant plaques are hybridized at 42° C. with two $^{32}P$-labelled oligonucleotide probes, one specific to the experimental leukemic cell, and one specific to the B or T cell line added as a tracer [Yamada et al, cited above]. The ratio of positive plaques in the two filters will give the relative frequency of the experimental ALL cells, as compared to the tracer population added in vitro. This number divided by 10 will give the number of leukemic cells present in the overall population.

Numerous modifications and variations of the present invention are included in the above-identified specification and are expected to be obvious to one of skill in the art. Such modifications and alterations to the methods of the present invention are believed to be encompassed in the scope of the claims appended hereto.

What is claimed is:

1. The immortalized cytotoxic T-ALL cell line, TALL-104 (ATCC No. CRL 11386).

* * * * *